(12) United States Patent
Taniguchi et al.

(10) Patent No.: US 10,408,826 B2
(45) Date of Patent: *Sep. 10, 2019

(54) CHEMICAL ANALYSIS APPARATUS, PRETREATMENT APPARATUS, AND CHEMICAL ANALYSIS METHOD

(71) Applicant: HITACHI, LTD., Tokyo (JP)

(72) Inventors: Shinichi Taniguchi, Tokyo (JP); Takahiro Ando, Tokyo (JP)

(73) Assignee: HITACHI, LTD., Tokyo (JP)

( * ) Notice: Subject to any disclaimer, the term of this patent is extended or adjusted under 35 U.S.C. 154(b) by 111 days.

This patent is subject to a terminal disclaimer.

(21) Appl. No.: 15/459,687

(22) Filed: Mar. 15, 2017

(65) Prior Publication Data

US 2018/0080930 A1 Mar. 22, 2018

(30) Foreign Application Priority Data

Sep. 16, 2016 (JP) ................................. 2016-182189

(51) Int. Cl.
*G01N 33/543* (2006.01)
*G01N 33/68* (2006.01)
(Continued)

(52) U.S. Cl.
CPC ... *G01N 33/54373* (2013.01); *B01D 15/3852* (2013.01); *G01N 30/14* (2013.01);
(Continued)

(58) Field of Classification Search
CPC ......... B01D 15/3852; G01N 2030/143; G01N 2030/8822; G01N 2600/00; G01N 30/14; G01N 30/7233; G01N 30/88; G01N 33/54366; G01N 33/54373; G01N 33/54386; G01N 33/6842; G01N 33/6848;
(Continued)

(56) References Cited

U.S. PATENT DOCUMENTS

| 2014/0227798 A1* | 8/2014 | Takeuchi | G01N 33/543 |
| | | | 436/501 |
| 2016/0091505 A1* | 3/2016 | Takeuchi | G01N 33/743 |
| | | | 436/501 |
| 2018/0196017 A1* | 7/2018 | Taniguchi | G01N 33/566 |

FOREIGN PATENT DOCUMENTS

| JP | 2006-204998 | * | 8/2006 |
| JP | 2011-027421 A | | 2/2011 |

(Continued)

OTHER PUBLICATIONS

Chen et al. Scientific Reports, vol. 5:11438, Jul. 1, 2015, pp. 1-12.*
(Continued)

*Primary Examiner* — Maureen Wallenhorst
(74) *Attorney, Agent, or Firm* — Baker Botts L.L.P.

(57) ABSTRACT

A chemical analysis apparatus that quantitatively determines an object of detection rapidly with high sensitivity, and a pretreatment apparatus and a chemical analysis method used for the chemical analysis apparatus, are provided. The chemical analysis apparatus includes a pretreatment unit that accommodates a molecularly imprinted polymer capable of capturing a polar group-containing molecule included in a specimen. A quantification unit quantitatively determines a component included in the specimen that has been passed through the pretreatment unit.

9 Claims, 5 Drawing Sheets

(51) Int. Cl.
*G01N 33/92* (2006.01)
*B01D 15/38* (2006.01)
*G01N 30/88* (2006.01)
*G01N 30/14* (2006.01)
*G01N 30/72* (2006.01)

(52) U.S. Cl.
CPC ....... *G01N 30/88* (2013.01); *G01N 33/54366* (2013.01); *G01N 33/54386* (2013.01); *G01N 33/6842* (2013.01); *G01N 30/7233* (2013.01); *G01N 33/6848* (2013.01); *G01N 33/92* (2013.01); *G01N 2030/143* (2013.01); *G01N 2030/8822* (2013.01); *G01N 2600/00* (2013.01); *Y10T 436/255* (2015.01); *Y10T 436/25125* (2015.01)

(58) Field of Classification Search
CPC ..... G01N 33/92; Y10T 436/16; Y10T 436/24; Y10T 436/25; Y10T 436/25125; Y10T 436/25375; Y10T 436/255
USPC ... 436/71, 86, 103, 161, 173, 174, 175, 177, 436/178; 422/68.1, 70, 527
See application file for complete search history.

(56) References Cited

FOREIGN PATENT DOCUMENTS

WO 2014/181662 * 11/2014
WO 2017046836 * 3/2017

OTHER PUBLICATIONS

Helling et al. Analytical Chemistry, vol. 83, Feb. 9, 2011, pp. 1862-1865.*
Haginaka et al. Analytica Chimica Acta, vol. 748, Aug. 23, 2012, pp. 1-8.*

* cited by examiner

F I G. 4
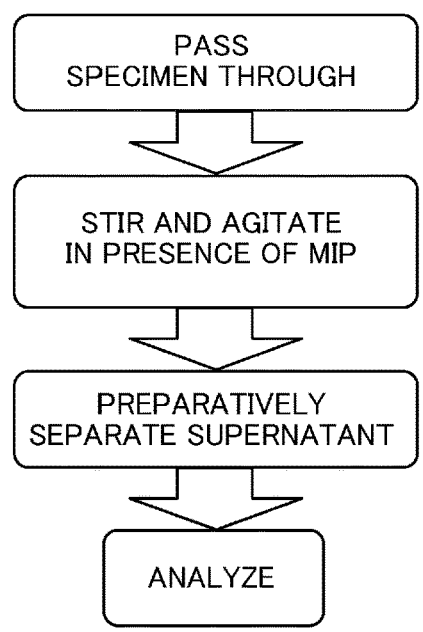
F I G. 5
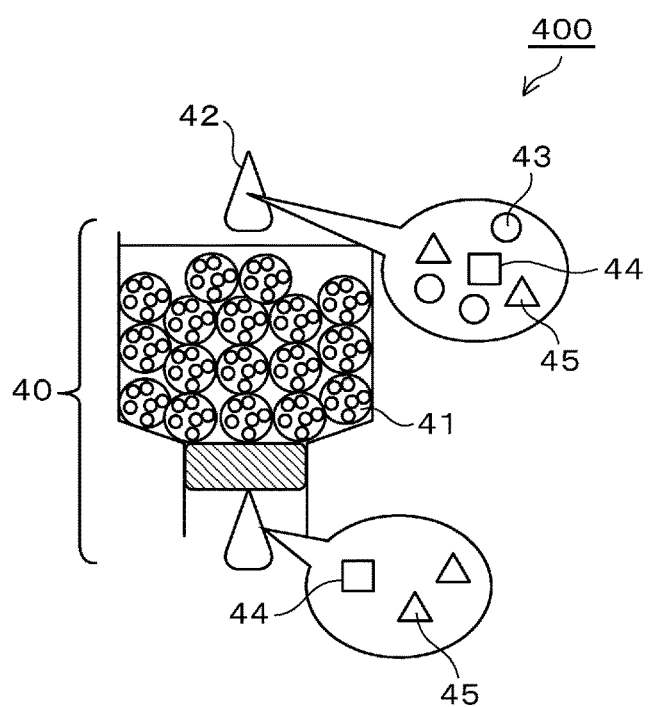

CHEMICAL ANALYSIS APPARATUS, PRETREATMENT APPARATUS, AND CHEMICAL ANALYSIS METHOD

CLAIM OF PRIORITY

The present application claims priority to Japanese Patent Application No. 2016-182189 filed on Sep. 16, 2016, the content of which is hereby incorporated by reference into this application.

TECHNICAL FIELD

The present disclosure relates to a chemical analysis apparatus, and to a pretreatment apparatus and a chemical analysis method used for this chemical analysis apparatus. More particularly, the presently disclosed subject matter relates to a chemical analysis apparatus used for the detection of biological molecules, and to a pretreatment apparatus and a chemical analysis method used for this chemical analysis apparatus.

BACKGROUND ART

There is a huge variety of diverse chemical substances that should be managed in the fields of clinical examination, environment, sanitation, disaster prevention, and the like. Examples thereof include hormone molecules; endocrine disruptors; soil pollutants in factory sites; asbestos generated from construction materials; and chemical substances that cause unpleasant odor or taste in foods, containers, or their production apparatuses. A significant number of such chemical substances are low molecular weight substances; they are usually included only in trace amounts in the materials to be analyzed. Detecting such trace amounts of chemical substances, rapidly with high sensitivity, is an extremely important operation for securing safety or the like in various fields.

For example, in the field of life-sciences, there has been a movement to acquire information that sensitively indicates the present, real-time status in the body by a metabolome analysis and then realize a tailor-made prophylaxis. In order to realize such a technique, it is required to analyze metabolites of relatively low molecular weights, such as amino acids and organic acids, and to apply the results to a diagnosis. Therefore, mass analysis is considered an important technology. Regarding a mass analysis apparatus, for example, it is known that mass spectrum is obtained by injecting a biological sample such as blood, serum, urine, or saliva into a vacuum under high voltage, and separating and detecting ionized components.

In the actual field of these analyses, there is a demand for an analysis technique that can detect a target chemical substance in situ with high sensitivity. Furthermore, in the actual field of analysis, there is also a demand for size reduction of the analysis apparatuses. In order to cope with these demands, when a particular chemical substance is selectively detected as an object of detection (hereinafter, also described as a "target molecule"), it is important to efficiently eliminate substances that disrupt detection (hereinafter, also described as "measurement inhibiting substances").

For example, Patent Document 1 discloses a reaction chip having, upstream from a reaction chamber, a pre-column unit that accommodates a carrier, which is capable of eliminating measurement inhibiting substances in a specimen. A specimen or a reagent is transported to this reaction chamber or pre-column unit using a centrifugal force caused by rotation.

CITATION LIST

Patent Document

Patent Document 1: JP 2011-27421 A

SUMMARY OF THE INVENTION

Problems to be Solved by the Invention

The reaction chip described in Patent Document 1 needs to have a fine structure for eliminating measurement inhibiting substances in a specimen or a mechanism for generating centrifugal force. The structure as a whole therefore becomes complicated. Further, in this reaction chip, since a specimen or a reagent is transported using centrifugal force caused by rotation, liquid transportation takes time, and this is not suitable for a high-throughput analysis.

Furthermore, in a mass analysis apparatus, there are occasions in which, for example, measurement inhibiting substances such as phospholipids that are included in a biological sample can be preferentially ionized from target molecules. In this case, there are occasions in which the target molecules that should be originally detected are not ionized and cause errors in the analysis results, so that the accuracy of analysis can be decreased.

Thus, it is an object of the present disclosure to provide a chemical analysis apparatus that quantitatively determines an object of detection rapidly with high sensitivity, and also to provide a pretreatment apparatus and a chemical analysis method used for this chemical analysis apparatus.

Solutions to Problems

An aspect of the present disclosure provides a chemical analysis apparatus having a pretreatment unit that accommodates a molecularly imprinted polymer and is capable of capturing a polar group-containing molecule included in a specimen; and a quantification unit that quantitatively determines a component that is included in the specimen as it is passed through the pretreatment unit.

Another aspect of the present disclosure provides a pretreatment apparatus that is used for a chemical analysis apparatus to quantitatively analyze components included in a specimen. The pretreatment apparatus includes a molecularly imprinted polymer capable of capturing a polar group-containing molecule included in the specimen. The polar group-containing molecule is eliminated from the specimen by the molecularly imprinted polymer.

Still another aspect of the present disclosure provides a chemical analysis method comprising passing a specimen through a pretreatment unit that accommodates a molecularly imprinted polymer capable of capturing a polar group-containing molecule; and quantitatively analyzing a component in the specimen passed through the pretreatment unit.

Effects of the Invention

The present disclosure relates to a chemical analysis apparatus that quantitatively determines an object of detection rapidly with high sensitivity, and to a pretreatment apparatus and a chemical analysis method used for the chemical analysis apparatus.

BRIEF DESCRIPTION OF THE DRAWINGS

FIG. 4 is a process flow chart including from a pretreatment step to an analysis step performed using a molecularly imprinted polymer.

FIG. 5 is a diagram illustrating a schematic configuration of a pretreatment apparatus 400 according to Embodiment 2.

MODE FOR CARRYING OUT THE INVENTION

[Embodiment 1]

Figure 1:
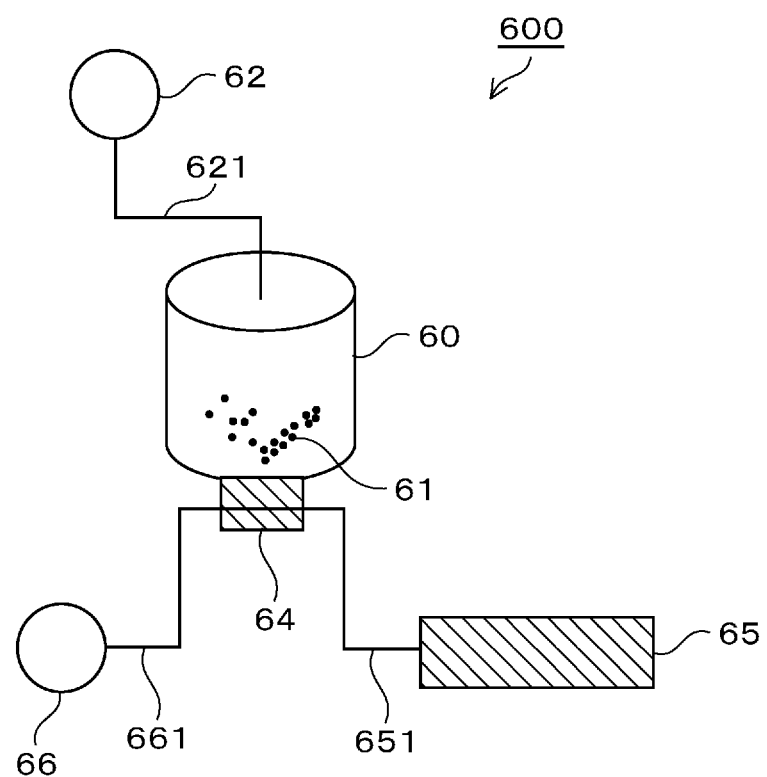
FIG. 1 is a diagram illustrating a schematic configuration of a chemical analysis apparatus 600 according to Embodiment 1.

FIG. 1 illustrates a schematic configuration of a chemical analysis apparatus 600 according to Embodiment 1. The chemical analysis apparatus 600 has a pretreatment unit 60 that accommodates molecularly imprinted polymer microparticles 61 in the inside. The molecularly imprinted polymer microparticles 61 contain a molecularly imprinted polymer that is capable of capturing a polar group-containing molecule included in a specimen as a measurement inhibiting substance. The molecularly imprinted polymer microparticles 61 contain a molecularly imprinted polymer that is capable of capturing a polar group-containing molecule included in a specimen as an analysis inhibiting substance. The molecularly imprinted polymer captures a particular measurement inhibiting substance in a specimen based on the particular molecular structure carried by that measurement inhibiting substance. Capturing as used herein means recognition as a result of binding or interaction.

The pretreatment unit 60 is configured to include, for example, glass or a resin such as polydimethyl sulfoxide (PDMS) or an acrylic resin. The molecularly imprinted polymer microparticles 61 have a function as a scavenger that captures a measurement inhibiting substance Details will be described below.

At the pretreatment unit 60, a specimen inlet portion 62 for introducing a specimen into the pretreatment unit 60 is connected to the pretreatment unit 60 by a flow channel 621. A drain 66 is further connected to the pretreatment unit 60 by a discharge flow channel 661, and a quantification unit 65 is connected to the pretreatment unit 60 by an outlet flow channel 651. The discharge flow channel 661 and the outlet flow channel 651 are connected in a switchable manner by a switching unit 64.

The quantification unit 65 quantitatively determines an object of detection (target molecule) included in a specimen that has been sent from the pretreatment unit 60. For example, a mass analysis apparatus, a liquid chromatography mass analysis apparatus, a liquid chromatograph, a spectrophotometer, or an automatic biochemical/immunological analyzer can be used.

When a specimen is injected into the pretreatment unit 60 from the specimen inlet portion 62 through the flow channel 621, a measurement inhibiting substance included in the specimen is captured by the molecularly imprinted polymer microparticles 61, and stays in the pretreatment unit 60. When the switching unit 64 is switched to the outlet flow channel 651 side, specimen solution that has been pretreated at the pretreatment unit 60 is sent to the quantification unit 65 by the outlet flow channel 651 via the switching unit 64, and is quantitatively analyzed for the object of detection (target molecule).

As a result, the specimen solution, in which the amount of the measurement inhibiting substance has been reduced to a large extent compared to the amount before passing through the pretreatment unit 60, can be quantitatively analyzed at the quantification unit 65. For this reason, a quantitative analysis of the target molecule can be performed rapidly with high sensitivity, and analysis results with a high signal/noise ratio (S/N) can be obtained.

The molecularly imprinted polymer microparticles 61 that have captured the measurement inhibiting substance, which remain in the pretreatment unit 60, can be discharged through the drain 66 via the discharge flow channel 661, together with unnecessary foreign materials, by switching the switching unit 64 over to the discharge flow channel 661 side from the outlet flow channel 651 side.

Furthermore, the chemical analysis apparatus of Embodiment 1 is intended mainly for low molecular weight chemical substances as target molecules. However, in some mass analysis apparatuses for clinical examination, in regard to the examination items, components having molecular weights that are close to those of such low molecular weight target molecules are dealt with as examination noise that inhibits measurement. In such chemical analysis apparatuses, efficient concentration of the target molecule and reduction of the measurement inhibiting substance dictate whether examination of an examination item can be carried out successfully. In the chemical analysis apparatus according to Embodiment 1, since measurement inhibiting substances included in a specimen can be efficiently eliminated by the pretreatment unit 60 having the molecularly imprinted polymer microparticles 61, the influence of the measurement inhibiting substances on the detection results thus obtainable can be reduced.

Additionally, for example, a mass analysis apparatus performs a component analysis for obtaining a mass spectrum related to the detection intensity with respect to the mass/charge ratio. This is done by injecting a biological sample, such as blood, serum, urine, or saliva, into a vacuum under high voltage, causing components that have been ionized in the vacuum to fly under electrostatic force, separating various components according to the mass/charge ratio as a result of electrical action or magnetic action, and respectively detecting the separated components.

For example, when serum components obtained by separating blood corpuscles from blood are subjected to a mass analysis using such a mass analysis apparatus, in any case where the serum components are directly injected into the mass analysis apparatus, and in cases in which serum components obtained after a pretreatment are injected into the mass analysis apparatus, phospholipids in the serum can enter into an ionizing pot together with the object of detection (target molecule). Since phospholipids are preferentially ionized, the object of detection (target molecule) that should be originally ionized does not undergo ionization, and errors in the measurement results have occurred.

In the chemical analysis apparatus of Embodiment 1, a quantitative analysis can be carried out by eliminating in advance measurement inhibiting substances that have polar groups prone to be ionized from a specimen by means of a molecularly imprinted polymer in the pretreatment unit 60, and then passing this specimen through the quantification unit 65. Therefore, in a case in which the quantification unit 65 is the mass analysis apparatus described above, deterioration of the accuracy of analysis caused by, for example, preferential ionization of measurement inhibiting substances having polar groups, such as phospholipids, can be prevented.

Furthermore, in a case in which the quantification unit 65 is, for example, a liquid chromatograph or a spectroscopic analyzer, the overlap between the peaks of the object of detection (target molecule) and the peaks of measurement inhibiting substances in the spectrum obtainable by mass analysis can be reduced.

Moreover, in a case in which the quantification unit 65 is, for example, an automatic biochemical/immunological analyzer, the occurrence of measurement errors caused by measurement inhibiting substances adhering onto a substrate having an antigen or an antibody attached thereto, or an inhibitory reaction against the antigen-antibody reaction caused by measurement inhibiting substances, can be prevented.

For the detection of a target molecule, measuring means using electrical measurement, impedance measurement, surface plasmon resonance, quartz oscillation or the like; a spectrophotometer; and the like can also be used as the quantification unit 65, in addition to the mass analysis apparatus described above.

FIG. 1 illustrates a configuration in which a quantification unit 65 is provided with one pretreatment unit 60; however, it is also possible to provide a plurality of pretreatment units 60 for one quantification unit 65. In this case, since elimination of measurement inhibiting substances can be carried out in parallel by a plurality of pretreatment units 60, a high-throughput analysis can be performed more efficiently.

The molecule that is captured by the molecularly imprinted polymer (hereinafter, described as "object molecule of capture") is a molecule that has a polar group and is prone to be ionized as described above. Examples thereof include molecules having phosphate groups, such as phospholipids, phospholipid derivatives, phosphoproteins, and phosphopeptides.

The molecular weight of the object molecule of capture is not particularly limited as long as the molecular weight can be captured by the scavenger; however, since a major purpose of Embodiment 1 lies in detection of low molecular weight chemical substances, the molecular weight of the target molecule is approximately several tens to several hundreds. This also applies to the following Embodiment 2.

Figure 2:
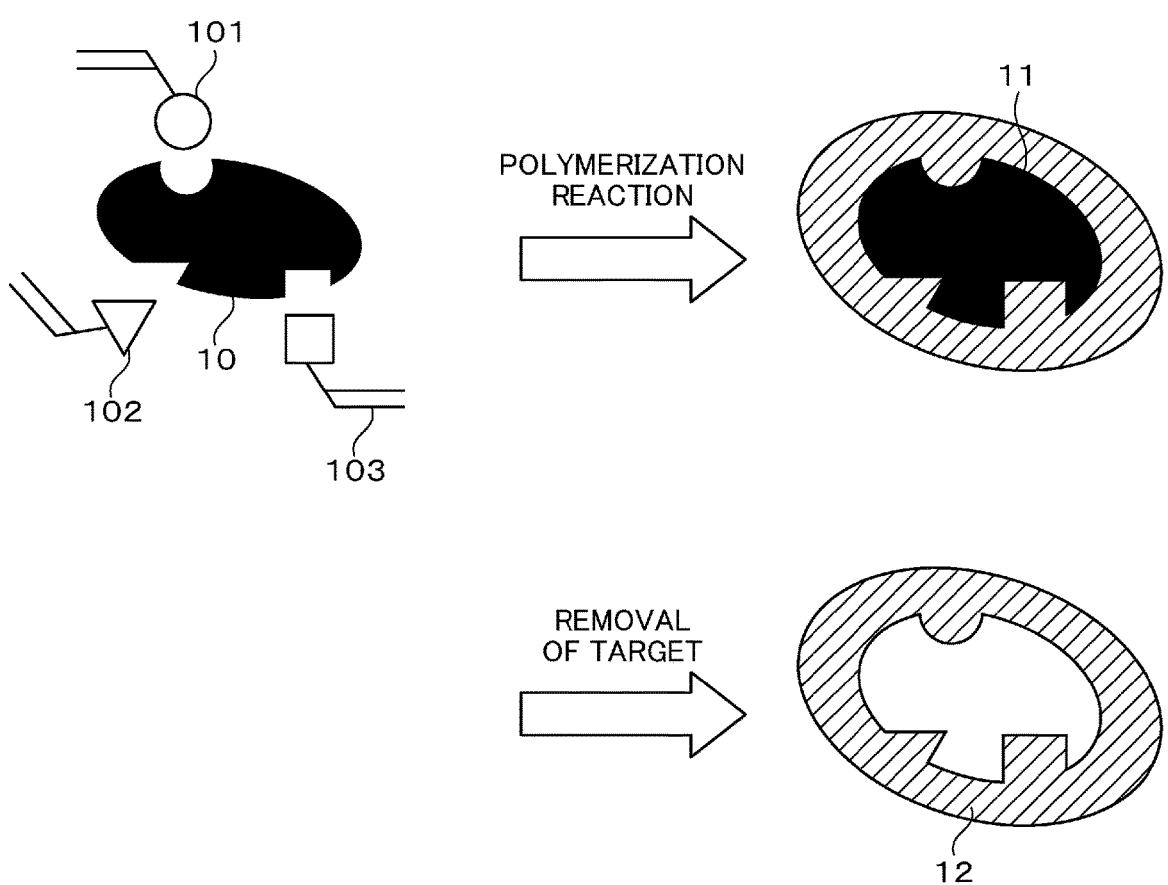
FIG. 2 is a diagram schematically illustrating a representative method for producing a molecularly imprinted polymer.

FIG. 2 illustrates a representative principle of production of a molecular imprinted polymer (MIP) 12 that is included in the molecularly imprinted polymer microparticles 61. First, a polymerization reaction is performed in a mixture of a template molecule 10 for an object molecule of capture with a monomer raw material 101, a monomer raw material 102, and a monomer raw material 103 that interact with this template molecule 10. A recognition site 11 of the template molecule 10 is formed. Subsequently, the template molecule 10 is removed by washing or the like, and thereby a molecularly imprinted polymer (MIP) 12 having a recognition site 11 can be produced.

The template molecule 10 is a template molecule for forming a recognition site 11, and the object molecule of capture itself can be used, or a derivative or analogue of the object molecule of capture can also be used.

The molecularly imprinted polymer (MIP) 12 is formed by utilizing a particular template molecule 10, and is capable of capturing a chemical substance that serves as an object molecule of capture, depending on the particular molecular structure of the object molecule of capture. A scavenger that captures the object molecule of capture can be any agent having at least the molecularly imprinted polymer (MIP) 12, and can have a material other than a polymer, which has a function of capturing the object molecule of capture depending on a particular molecular structure. For example, the scavenger can be a protein, or can be a metal. Specifically, an antibody, a molecularly imprinted polymer and the like are classified as scavengers.

A non-limiting method for producing the molecularly imprinted polymer (MIP) 12 is as follows. For example, first, in the presence of a template molecule 10, which is an object molecule of capture or a chemical substance analogous thereto, a functional monomer that interacts with the template molecule 10 by ionic bonding or hydrogen bonding, is polymerized together with another monomer component that is used as necessary, forming a polymer. Thus, the template molecule 10 is immobilized within the polymer. At that time, the copolymerization ratio between the functional monomer and the other monomer component can vary depending on the kind of the various monomer components or the like, and is not particularly limited. However, for example, the copolymerization ratio can be set so as to satisfy the following condition: functional monomer:other monomer component=1:16 to 1:64 (molar ratio). Particularly, the ratio of functional monomer:other monomer component=1:32 is desirable. Subsequently, the template molecule 10 is removed from the polymer by washing. The cavity (space) remaining in the polymer memorizes the shape of the template molecule 10, and also serves as a recognition site having a chemical recognition ability due to the functional monomer immobilized within the molecularly imprinted polymer (MIP) 12.

Regarding the template molecule 10, for example, a substance obtained by derivatizing the object molecule of capture and introducing a functional group that undergoes a copolymerization reaction with the monomers that form the molecularly imprinted polymer, can also be used. When covalent bonds are formed by a copolymerization reaction between the template molecule 10 and the monomers, the interaction between the two parties becomes stronger, and fitting properties between the template molecule 10 and the monomers are enhanced. Thereby, the molecularly imprinted polymer (MIP) 12 acquires advantageous characteristics such as increased intake efficiency for the object molecule of capture. Regarding the monomers that are copolymerized with such derivatized object molecule of capture, a monomer having two or more functional groups, or a combination of multiple kinds of monomers can be used, similar to the raw material monomers in the case of using a non-derivatized object molecule of capture as the template molecule 10.

Furthermore, examples of functional groups that undergo a copolymerization reaction with monomers, and is introduced into the template molecule 10, include polymerizable substituents such as an acryloyl group, a methacryloyl group, a vinyl group, and an epoxy group. Particularly, a methacryloyl group is preferred.

The object molecule of capture is meant to also include a chemical substance that can exist in the solid state only at normal temperature and normal pressure, and can exist as microparticles in a gas or a liquid. However, chemical substances having a corrosive effect, a dissolving effect, a denaturing effect or the like on the molecularly imprinted polymer are not suitable as the object molecule.

Generally, when a molecularly imprinted polymer is produced, as described above, a recognition site (space) for capturing an object molecule of capture is formed by synthesizing the molecularly imprinted polymer using the object molecule of capture or a derivative thereof as the template molecule, and then removing the template molecule by washing. However, the molecularly imprinted polymer synthesized as described above has a possibility that the template molecule can remain in the polymer even after washing. When such a molecularly imprinted polymer is used for a pretreatment of a specimen, any template molecule remaining in the molecularly imprinted polymer can be eluted into the specimen after the pretreatment and can flow into the quantification unit 65 (see FIG. 1). In this case, if the template molecule 10 that has flowed into the quantification unit 65 is a measurement inhibiting substance causing disruption of the examination results, the accuracy of analysis obtainable by the quantification unit 65 is decreased.

Therefore, in a case in which the object molecule of capture is a measurement inhibiting substance that disrupts the analysis results, even if only a trace amount of the object molecule of capture remains in the specimen, such as a phospholipid for example, it is preferable to produce the molecularly imprinted polymer using a molecule other than the object molecule of capture or a derivative thereof as the template molecule.

For example, in a case in which the object molecule of capture is a molecule having a phosphate group, it is preferable to synthesize the molecularly imprinted polymer using a molecule different from this object molecule of capture, i.e., a molecular not having a phosphate group, as the template molecule 10. In this case, regarding the template molecule 10, a molecule which imitates the molecular structure of a molecule having a phosphate group and has a polar group in the molecule, where the polar group has on either side a site of binding to another atomic group, can be used.

For example, in a case in which a molecularly imprinted polymer for capturing a phospholipid is synthesized, it is preferable to use a molecule which imitates a molecular structure of the phospholipid, as the template molecule 10, instead of using a phospholipid or a derivative thereof. As the molecule that imitates the molecular structure of a phospholipid, a molecule having a ketoprofen skeleton can be used from the viewpoint of molecular structure, functional group or the like, e.g., S-ketoprofen.

Specifically, a molecularly imprinted polymer can be obtained by copolymerizing a vinyl monomer as a functional monomer, and optionally another monomer component such as styrene or divinylbenzene, together with a polymerization initiator, in the presence of S-ketoprofen as a template molecule 10.

In a case in which a vinyl monomer as the functional monomer and another monomer component are copolymerized as described above, the copolymerization ratio can vary depending on the various monomer components, the kind of the template molecule, or the like, and the copolymerization ratio is not particularly limited.

The molecularly imprinted polymer obtained as such has a recognition site that can be specifically bound to a molecule having a ketoprofen skeleton. As described above, since the ketoprofen skeleton is a molecular structure that imitates the molecular structure of phospholipids, this recognition site functions as the recognition site for phospholipids.

In a case in which S-ketoprofen is used as the template molecule 10, a substance that has been derivatized by introducing, for example, a polymerizable substituent such as an acryloyl group, a methacryloyl group, a vinyl group, or an epoxy group into S-ketoprofen, can be used.

Meanwhile, the molecularly imprinted polymer can be any polymer produced by performing a polymerization reaction in the presence of a template molecule. The interaction between the template molecule and a vinyl monomer in the surroundings is not limited to covalent bonding, and some of ionic bonding, hydrogen bonding, van der Waals force, hydrophobic-hydrophobic bonding and the like, or combinations thereof can also be utilized.

Figure 3A:
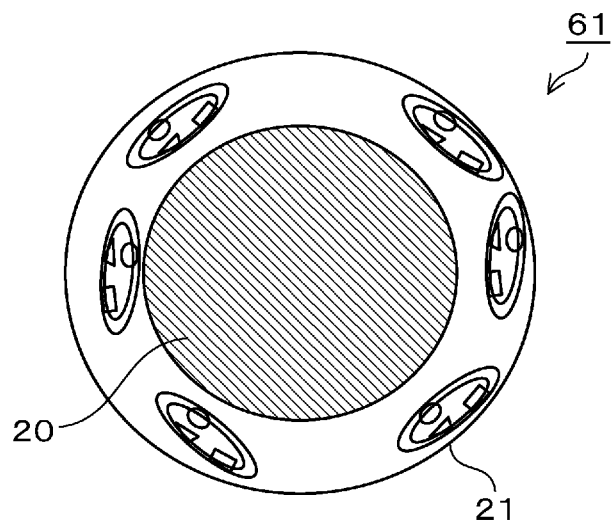
FIG. 3A is a diagram schematically illustrating a cross-section of a molecularly imprinted polymer microparticle 61.
Figure 3B:
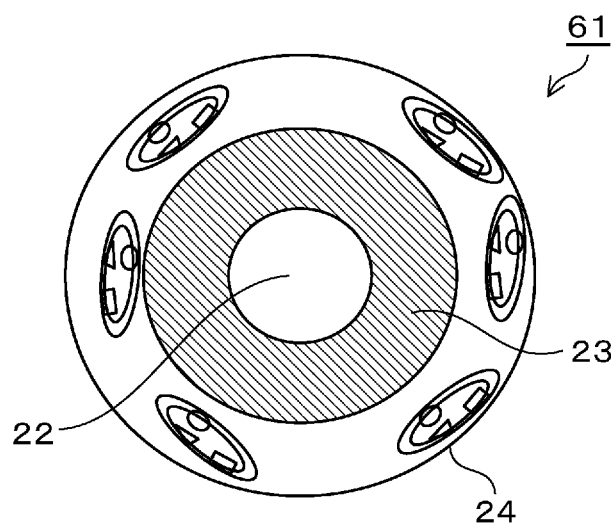
FIG. 3B is a diagram schematically illustrating a cross-section of a molecularly imprinted polymer microparticle 61.

FIG. 3A and FIG. 3B illustrate cross-sectional views of a molecularly imprinted polymer microparticle 61 accommodated in the pretreatment unit 60. The molecularly imprinted polymer microparticle 61 has a core-shell type bilayer structure having a shell layer 21 around a core layer 20.

A core-shell type molecularly imprinted polymer microparticle can be produced into, for example, as illustrated in FIG. 3A, a microparticle structure in which a polystyrene layer is used as the core layer 20, and a layer of the molecularly imprinted polymer is formed as the shell layer 21. A molecularly imprinted polymer microparticle having such a core-shell structure is submicron-sized, and since the particle size is uniform, when the particles are arranged in a column shape or a flat plate shape, the particles can be packed compactly. Thus, high recognition power for the target molecule is obtained.

Regarding the shell layer 21, the particle can have a layer of a molecularly imprinted polymer that captures a measurement inhibiting substance as a surface layer, on the outer side of the core layer 20. In other words, it is desirable if a particle having a layer of a molecularly imprinted polymer that captures a measurement inhibiting substance as a surface layer can be synthesized.

The molecularly imprinted polymer microparticle 61 is not limited to a core-shell type microparticle having a bilayer structure, which has a shell layer 21 around a core layer 20 (see FIG. 3A). A core-shell 1-shell 2-type microparticle having a trilayer structure can also be used. A core-shell 1-shell 2-type molecularly imprinted polymer microparticle 61 having a trilayer structure has a core-shell 1-shell 2-type structure having a first shell layer 23 around a core layer 22, and having a second shell layer 24 around the first shell layer 23, as illustrated in FIG. 3B. When such a structure is adopted, for example, a $Fe_2O_3$ (iron oxide) bead is used as the core layer 22, a polystyrene layer is formed as the first shell layer 23, and a layer of a molecularly imprinted polymer is formed as the second shell layer 24. Thereby, molecularly imprinted polymer microparticles having magnetic properties can be produced.

Herein, an example of using $Fe_2O_3$ (iron oxide) as the core layer 22 of the molecularly imprinted polymer microparticles 61 is described; however, a magnetic material other than $Fe_2O_3$ (iron oxide) can also be used as the core layer 22.

The molecularly imprinted polymer microparticles 61 function as a magnetic material, and after measurement inhibiting substances are captured by the surface layer, for example, the molecularly imprinted polymer microparticles 61 can be moved by means of a magnet or the like. Thus, handling is made easier. Specifically, for example, a magnetic material having the molecularly imprinted polymer in the surface layer is immersed in a specimen containing an object of detection (target molecule) together with measurement inhibiting substances, such as blood serum or urine. The magnetic material is left to stand therein for a certain time, the measurement inhibiting substances are captured by the molecularly imprinted polymer, and then this magnetic material can be easily pulled up from the specimen using a magnet or the like. As a result, the measurement inhibiting substances can be separated from among the substances included in the specimen.

Above all, the core-shell 1-shell 2-type molecularly imprinted polymer microparticles can have increased adhesiveness between the layer of the molecularly imprinted polymer as the second shell layer 24 and the $Fe_2O_3$ (iron oxide) bead as the core layer 22 by means of the polystyrene layer as the first shell layer 23. A stable molecule capturing function can be obtained due to the molecularly imprinted polymer.

A synthesis scheme for core-shell type molecularly imprinted polymer microparticles is illustrated below. A polymerization reaction is performed in the presence of microparticles containing the component that forms a core layer 22 (hereinafter, simply described as "core beads"), and the product is subjected to centrifugation, hydrolysis, and washing. Thus, polymer beads having a molecularly imprinted polymer on the surface can be synthesized.

That is, there is a feature that microparticles of the molecularly imprinted polymer can be produced by subjecting a template molecule 10 and a polymerizable vinyl monomer (functional monomer) to a polymerization reaction in the presence of core beads (microparticles). Subsequently, the microparticles are subjected to a centrifugation process, a hydrolysis process, and a washing process, and finally, microparticles of the molecularly imprinted polymer can be obtained.

In regard to the molecularly imprinted polymer microparticles obtained as described above, the core beads (microparticles) are coated with a molecularly imprinted polymer that is synthesized using raw material monomers of the molecularly imprinted polymer and a template molecule 10 (object molecule of capture or a derivative thereof). The molecularly imprinted polymer that coats the core beads (microparticles) has a recognition site for the object molecule of capture.

For example, when the polystyrene beads are used as core beads, and a polymerization reaction, centrifugation, hydrolysis, and washing are performed as described above, the core-shell type molecularly imprinted polymer microparticles having a bilayer structure as illustrated in FIG. 3A can be synthesized.

Furthermore, for example, when $Fe_2O_3$ (iron oxide) beads are used as core beads, a polystyrene layer is formed in advance on the surface of the beads, and a polymerization reaction, centrifugation, hydrolysis, and washing are performed as described above, the core-shell 1-shell 2-type molecularly imprinted polymer microparticles having a trilayer structure as illustrated in FIG. 3B can be synthesized.

In the chemical analysis apparatus of Embodiment 1 explained above, since a quantitative analysis can be performed after a measurement inhibiting substance, such as a phospholipid that disrupts analysis, is eliminated by the molecularly imprinted polymer, a high precision analysis can be carried out.

Furthermore, in the chemical analysis apparatus of Embodiment 1, since a measurement inhibiting substance can be continuously eliminated by using a molecularly imprinted polymer, without using a complicated apparatus configuration or a large-scale apparatus configuration, a high-throughput analysis can be carried out efficiently at low cost.

FIG. 4 illustrates an example of the process flow when processes including from the pretreatment step to the analysis step are carried out using the molecularly imprinted polymer (MIP) described above. First, a specimen as an object of examination is passed through a vial, a syringe, a column or the like, which is packed with a molecularly imprinted polymer (MIP) 12. At this time, in the presence of the specimen and the molecularly imprinted polymer (MIP) 12, these substances are stirred and agitated. Thereby, a measurement inhibiting substance in the specimen can be effectively captured by the molecularly imprinted polymer (MIP) 12. Subsequently, a supernatant of the suspension obtained by stirring of a specimen and a molecularly imprinted polymer (MIP) is preparatively separated. Then, the components included in the supernatant thus separated are analyzed.

Since measurement inhibiting substances such as, for example, phospholipids, are eliminated from a specimen solution by the process flow described above, a high sensitivity analysis of a target molecule is enabled.

[Embodiment 2]

FIG. 5 illustrates a schematic configuration of a pretreatment apparatus 400 according to Embodiment 2. The pretreatment apparatus 400 can be applied to, for example, the pretreatment unit 60 of the chemical analysis apparatus 600 illustrated in FIG. 1, and thus the pretreatment apparatus 400 includes a syringe-like vessel 40. The vessel 40 is packed with a molecularly imprinted polymer 41 that captures phospholipids 43. Regarding the molecularly imprinted polymer 41, a polymer similar to the molecularly imprinted polymer described in Embodiment 1 can be used. The specimen 42 includes phospholipids 43 that become measurement inhibiting substances. Also, the specimen 42 includes a molecule 44 or a molecule 45, which are both objects of detection (target molecules).

First, this specimen 42 is passed through the vessel 40. Phospholipids 43 in the specimen 42 that has passed through the vessel 40 are captured by the molecularly imprinted polymer 41 and are eliminated. When the specimen 42 after being pretreated as such is analyzed, an accurate analysis can be carried out.

FIG. 5 illustrates an example of capturing and eliminating phospholipids 43 in a specimen by means of the molecularly imprinted polymer 41. However, the pretreatment apparatus 400 is capable of eliminating measurement inhibiting substances other than phospholipids, such as phospholipid derivatives, phosphoproteins, and phosphopeptides by appropriately selecting the kind of the molecularly imprinted polymer 41.

In Embodiment 1 and Embodiment 2 described above, cases of using molecularly imprinted polymer microparticles have been explained as examples. Regarding the scavenger for the measurement inhibiting substances, a pulverized molecularly imprinted polymer having a small particle size and an aligned particle size, which is obtained by pulverizing and classifying a powder obtained after synthesis of a molecularly imprinted polymer, can also be used. However, in order to increase the sensitivity of detection of a target molecule, a larger surface area of the molecularly imprinted polymer is more suitable. Therefore, in order to further reduce the particle size of the scavenger, as described above, it is preferable to use a molecularly imprinted polymer microparticles obtained by coating the surface of core beads having a particle size on the order of submicrons with a molecularly imprinted polymer.

Furthermore, according to Embodiment 1 and Embodiment 2 described above, when molecularly imprinted polymer microparticles having a molecularly imprinted polymer as a scavenger for a measurement inhibiting substance are used, a quantitative analysis of an object of detection (target molecule) can be carried out rapidly without using a highly expensive apparatus such as a separatory apparatus (HPLC), which has been conventionally needed for quantitative analyses. Therefore, the molecularly imprinted polymer microparticles can contribute to general cost reduction or size reduction for chemical analysis apparatuses. Off-line separation can also be adopted.

EXPERIMENTAL EXAMPLE 1

Next, a method for producing a molecularly imprinted polymer will be explained in more detail. In the following description, a molecularly imprinted polymer microparticles for capturing phospholipids, which are measurement inhibiting substances disrupting a chemical analysis, will be explained according to the procedure described above.

(Synthesis of Molecularly Imprinted Polymer Microparticles)

In Experimental Example 1, a molecularly imprinted polymer capable of capturing phospholipids was synthesized using S-ketoprofen as a template molecule.

Specifically, as described below, a pulverized type molecularly imprinted polymer was synthesized. First, S-ketoprofen (0.10 mmol/L, 259 mg) as a template molecule, MAA (0.48 mmol/L, 410 μL), EDMA (1.56 mmol/L, 2.95 μL), 4-styrenesulfonic acid (100 mg), and AIBN (17.5 mg) were dissolved in 50 mL of a solvent (acetonitrile: 45 mL, ion-exchanged water: 5 mL). Next, the vessel was capped with a septum and was purged with nitrogen. After nitrogen purging for 10 minutes, the solution was allowed to react for 12 hours at 70° C.

The polymerization liquid was collected and supplied to a centrifuge to remove supernatant solution. Subsequently, the residue was subjected to Soxhlet washing. Specifically, the residue was washed with methanol/acetic acid=9:1 through Soxhlet washing, and then was washed with methanol.

A molecularly imprinted polymer for removing phospholipids could be produced by the method described above. In order to confirm that ketoprofen had been sufficiently eliminated from the molecular imprinted polymer by the Soxhlet washing, the concentration of ketoprofen was measured by HPLC during the process of Soxhlet washing. The measurement results are presented in Table 1.

TABLE 1

| Solvent | Washing time (hour) | Ketoprofen concentration (ppm) | Amount of ketoprofen extracted (mg) |
|---|---|---|---|
| Acetic acid/methanol (9/1) | 8 | 11.1 | 110.5 |
|  | 16 | 2.3 | 22.6 |
|  | 24 | 0.6 | 6.3 |
| Methanol | 8 | 0.5 | 3.2 |
|  | 16 | 0.2 | 1.3 |
|  | 24 | ND | — |

EXPERIMENTAL EXAMPLE 2

Figure 6:
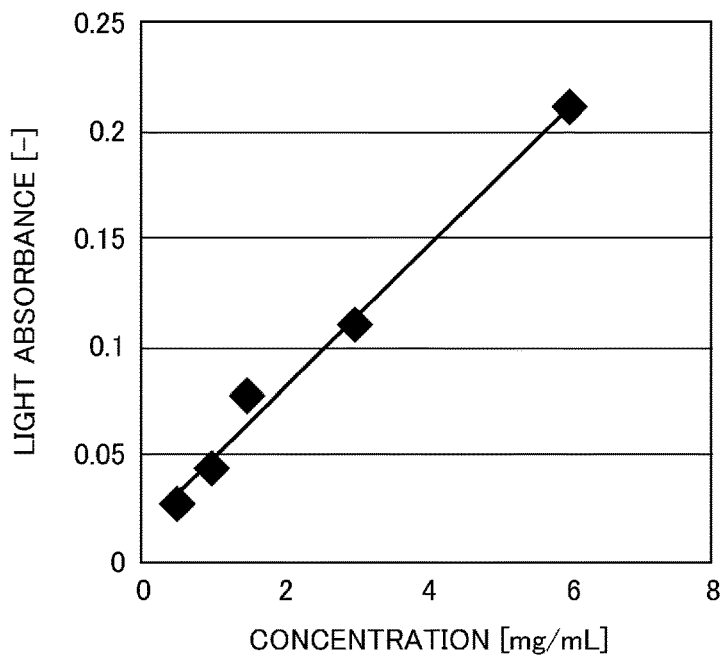
FIG. 6 is a diagram illustrating the relation between phospholipid concentration and light absorbance.

Phospholipid removal capability was evaluated using the molecularly imprinted polymer (MIP) synthesized in Experimental Example 1. First, light absorbance was measured at various phospholipid concentrations as a preliminary control. The measured values of light absorbance at various phospholipid concentrations are presented in Table 2. These measured values of light absorbance were plotted against various phospholipid concentrations, and a calibration curve was produced. Thus, the relation between phospholipid concentration and light absorbance was calculated. For the production of the calibration curve, 1-palmitoyl-2-oleoyl-sn-glycero-3-PC (1,2-POPC, 1-palmitoyl-2-oleoyl-sn-glycero-3-phosphocholine) was used as the phospholipid. FIG. 6 illustrates the relation between phospholipid concentration and light absorbance. As illustrated in FIG. 6, the plot of the light absorbance at various phospholipid concentrations shows a linear correlation. When the phospholipid concentration was designated as x, and the light absorbance as y, this relationship was approximated by the calculation formula: $y=0.0324x+0.0165$, and the coefficient of correlation was such that $R2=0.9894$.

TABLE 2

| Phospholipid concentration (mg/ml) | Light absorbance |
|---|---|
| 0.5 | 0.028 |
| 1 | 0.044 |
| 1.5 | 0.078 |
| 3 | 0.111 |
| 6 | 0.21 |

Next, an aqueous solution of a phospholipid was prepared so as to obtain a phospholipid concentration of 1.5 mg/mL, and this aqueous solution was dispensed into five vials in an amount of 1 mL each. The same phospholipid as that used for the production of the calibration curve of FIG. 6 was used. Next, the molecularly imprinted polymer (MIP) synthesized in Experimental Example 1 was introduced into each of the vials containing the aqueous solution of phospholipid, in an amount of 10 mg, 20 mg, 30 mg, 40 mg, and 50 mg, respectively. The vials were stirred and agitated for 60 minutes under the conditions of a temperature of 25° C. and 400 rpm. Subsequently, a suspension thus obtained was centrifuged, and the light absorbance of the supernatant was analyzed using an ELISA kit for quantitative determination of phospholipids (removal capability evaluation experiment).

Figure 7:
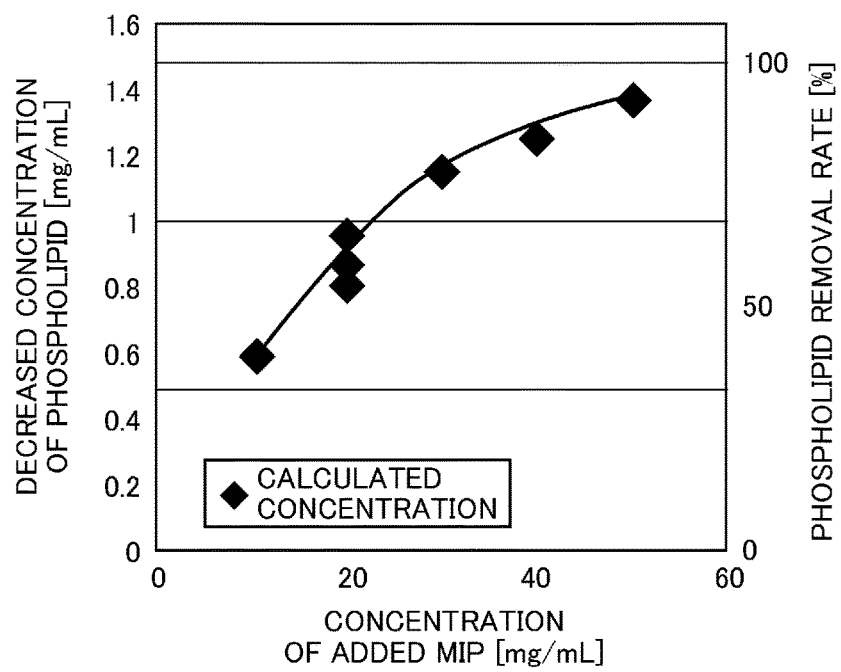
FIG. 7 is a diagram illustrating the relation between concentration of an added molecularly imprinted polymer and decreased concentration of a phospholipid.

The phospholipid concentrations of the various supernatants were calculated from the various light absorbances obtained by the above-described removal capability evaluation experiment using the calibration curve of FIG. 6. The decreased phospholipid concentration (decrement of the phospholipid concentration) and the removal rate were calculated. The decreased phospholipid concentration is the difference between each phospholipid concentration after the removal capability evaluation experiment and the initial concentration (1.5 mg/mL). The decreased phospholipid concentrations and the phospholipid removal rates at various molecularly imprinted polymer (MIP) concentrations are presented in Table 3. Furthermore, the relation between added molecularly imprinted polymer (MIP) concentration and decreased phospholipid concentration is presented in FIG. 7. In FIG. 7, the horizontal axis (x-axis) represents the concentration of added molecularly imprinted polymer (MIP) [mg/mL], the first vertical axis represents the decreased phospholipid concentration [mg/mL], and the second vertical axis represents the phospholipid removal rate [%] corresponding to the first vertical axis.

As illustrated in FIG. 7, the decreased phospholipid concentration, that is, the phospholipid removal rate, increased with an increase in the amount of addition of the molecularly imprinted polymer (MIP), and at an amount of addition of 50 mg, a removal rate of 90% or higher was achieved.

TABLE 3

| Added MIP concentration [mg/mL] | Decreased phospholipid concentration [mg/mL] | Phospholipid removal rate [%] |
| --- | --- | --- |
| 10.02 | 0.590 | 39.3 |
| 19.98 | 0.867 | 57.8 |
| 20.03 | 0.806 | 53.7 |
| 20.04 | 0.960 | 64.0 |
| 30.03 | 1.145 | 76.3 |
| 29.98 | 1.145 | 76.3 |
| 29.98 | 1.145 | 76.3 |
| 40.02 | 1.238 | 82.5 |
| 50.04 | 1.361 | 90.7 |

The invention claimed is:

1. A chemical analysis apparatus, comprising:
a specimen inlet connected to a pretreatment unit, wherein the specimen inlet is configured to introduce a specimen into the pretreatment unit, wherein the pretreatment unit contains a molecularly imprinted polymer capable of capturing a polar group-containing molecule included in a specimen; and
a drain and a quantification unit connected to the pretreatment unit by a switching unit, wherein the quantification unit is configured to quantitatively determine a component other than the polar group-containing molecule included in the specimen that has been passed through the pretreatment unit.

2. The chemical analysis apparatus according to claim 1, wherein the pretreatment unit captures at least one selected from the group consisting of a phospholipid, a phospholipid derivative, a phosphoprotein, and a phosphopeptide as the polar group-containing molecule by means of the molecularly imprinted polymer.

3. The chemical analysis apparatus according to claim 1, wherein the pretreatment unit contains molecularly imprinted polymer microparticles having the molecularly imprinted polymer on a surface.

4. The chemical analysis apparatus according to claim 1, wherein the pretreatment unit contains a polymer having a recognition site capable of specifically binding to a molecule having a ketoprofen skeleton as the molecularly imprinted polymer.

5. The chemical analysis apparatus according to claim 1, wherein the quantification unit is a mass analysis apparatus, a liquid chromatograph, or a liquid chromatography mass analysis apparatus.

6. A chemical analysis system, comprising:
a pretreater containing a molecularly imprinted polymer capable of capturing a polar group-containing molecule included in a specimen, wherein the polar group-containing molecule is eliminated from the specimen when the molecularly imprinted polymer captures the polar group-containing molecule;
a specimen inlet connected to the pretreater, wherein the specimen inlet is configured to introduce the specimen into the pretreater; and
a drain and a quantification unit connected to the pretreater by a switching unit.

7. The chemical analysis system according to claim 6, wherein the pretreater eliminates at least one selected from the group consisting of a phospholipid, a phospholipid derivative, a phosphoprotein, and a phosphopeptide as the polar group-containing molecule by means of the molecularly imprinted polymer.

8. A chemical analysis method, comprising:
introducing a specimen from a specimen inlet to a pretreater;
passing the specimen through the pretreater, wherein the pretreater contains a molecularly imprinted polymer capable of capturing a polar group-containing molecule in the specimen;
passing the specimen from the pretreater to a quantitative unit connected to the pretreater by a switching unit; and
quantitatively analyzing, by the quantitative unit, a component other than the polar group-containing molecule included in the specimen that has been passed through the pretreater, wherein a drain is also connected to the pretreater by the switching unit.

9. The chemical analysis method according to claim 8, wherein a specimen is passed through the pretreater that contains a molecularly imprinted polymer capable of capturing at least one selected from the group consisting of a phospholipid, a phospholipid derivative, a phosphoprotein, and a phosphopeptide as the polar group-containing molecule.

* * * * *